US011800973B2

(12) United States Patent
Pichereau et al.

(10) Patent No.: US 11,800,973 B2
(45) Date of Patent: Oct. 31, 2023

(54) VISUAL TEST METHOD, ASSOCIATED CONTROL MODULE AND SYSTEM

(71) Applicant: SiVIEW, Marcoussis (FR)

(72) Inventors: Laure Pichereau, Marcoussis (FR); Nathalie Guillemain, Saint Leu la Foret (FR)

(73) Assignee: SIVIEW, Marcoussis (FR)

( * ) Notice: Subject to any disclaimer, the term of this patent is extended or adjusted under 35 U.S.C. 154(b) by 709 days.

(21) Appl. No.: 16/971,903

(22) PCT Filed: Feb. 21, 2019

(86) PCT No.: PCT/EP2019/054374
§ 371 (c)(1),
(2) Date: Aug. 21, 2020

(87) PCT Pub. No.: WO2019/162412
PCT Pub. Date: Aug. 29, 2019

(65) Prior Publication Data
US 2021/0100446 A1 Apr. 8, 2021

(30) Foreign Application Priority Data
Feb. 23, 2018 (FR) ...................................... 1851618

(51) Int. Cl.
*A61B 3/032* (2006.01)
*A61B 3/00* (2006.01)

(52) U.S. Cl.
CPC ............ *A61B 3/032* (2013.01); *A61B 3/0033* (2013.01); *A61B 3/0041* (2013.01)

(58) Field of Classification Search
CPC ...... A61B 3/032; A61B 3/0033; A61B 3/0041
(Continued)

(56) References Cited

U.S. PATENT DOCUMENTS

| 2012/0092621 A1* | 4/2012 | Ozaki | A61B 3/028 351/222 |
| 2012/0092622 A1* | 4/2012 | Hirayama | A61B 3/032 351/240 |
| 2012/0212706 A1 | 8/2012 | Chou et al. | |

FOREIGN PATENT DOCUMENTS

| EP | 1 844 701 A1 | 10/2007 | |
| WO | WO-0191630 A2 * | 12/2001 | ............. A61B 3/032 |

(Continued)

OTHER PUBLICATIONS

International Search Report as issued in International Patent Application No. PCT/EP2019/054374, dated May 28, 2019.

*Primary Examiner* — James R Greece
(74) *Attorney, Agent, or Firm* — Pillsbury Winthrop Shaw Pittman LLP

(57) ABSTRACT

An eyesight testing method as well as to an associated control module and an associated system such that when the control module receives a selection of a test symbol, the control module selects the test symbol by modifying at least one appearance-related feature of the test symbol such that the test symbol changes from an initial appearance to a modified appearance that distinguishes same from non-selected test symbols; when a first predetermined time has elapsed since the last selection of a test symbol or since the display of the test symbol or the plurality of test symbols, the control module modifies at least one appearance-related feature of the validation symbol; the control module terminates the eyesight testing method as soon as a predetermined number of test symbols has been selected.

10 Claims, 3 Drawing Sheets

(58) Field of Classification Search
USPC ............... 351/222, 227, 229, 233, 237, 239
See application file for complete search history.

(56) References Cited

FOREIGN PATENT DOCUMENTS

| WO | WO 02/00105 A1 | 1/2002 | |
|---|---|---|---|
| WO | WO-2008012649 A2 * | 1/2008 | ........... A61B 3/0041 |
| WO | WO 2011/135364 A2 | 11/2011 | |
| WO | WO 2017/070704 A2 | 4/2017 | |

* cited by examiner

VISUAL TEST METHOD, ASSOCIATED CONTROL MODULE AND SYSTEM

CROSS-REFERENCE TO RELATED APPLICATIONS

This application is the U.S. National Stage of PCT/EP2019/054374, filed Feb. 21, 2019, which in turn claims priority to French patent application number 1851618 filed Feb. 23, 2018. The content of these applications are incorporated herein by reference in their entireties.

TECHNICAL FIELD OF THE INVENTION

The field of the invention is that of eyesight examinations which, conducted on a subject, make it possible to determine if said subject needs a correction and which correction.

The invention more specifically pertains to a visual test method for example during an eyesight examination, by means of a support which is either a refractor head, automatic or manual, or a pair of test glasses, and making it possible to objectivise a visual acuity measurement. The invention also relates to a control module for the implementation of the visual test method as well as a system comprising the control module, a selection screen and a reading screen for the implementation of the visual test method.

PRIOR ART

An eyesight examination of a subject starts by an objective refraction measurement and continues by a subjective refraction measurement.

The objective refraction measurement is generally carried out by means of an autorefractometer. Alternatively to the use of an autorefractometer, a manual skiascopy technique is sometimes used. Failing this, the operator may start from the preceding correction of the examined subject.

During the subjective refraction measurement, the operator has different visual corrections tested by the examined subject by means of suitable equipment which may be:
  a pair of test glasses with test lenses,
  a manual refractor head or
  an automatic refractor head.

In the first case, the operator manually changes the test lenses of the pair of test glasses. With a refractor head, the operator scrolls different lenses in front of the eyes of the examined subject, by means of thumbwheels in the case of a manual refractor head or via a control console in the case of an automatic refractor head.

In the course of such a subjective refraction measurement, the operator successively measures the visual acuity of the examined subject as a function of different tested visual corrections. More generally, measuring the visual acuity of an examined subject having a given visual correction is one step of numerous visual tests.

The operator arranges an optical lens in front of one eye of the examined subject (monocular case) or in front of both eyes of the examined subject (binocular case) while said subject observes a reading screen on which one or more test symbols are displayed. The test symbol(s) are generally letters or drawings. The operator asks the examined subject to recognise the test symbol(s). The operator validates or not the test underway as a function of the responses given by the examined subject. A visual acuity measurement is carried out in the monocular test (only one of the two eyes tested) or in the binocular test (both eyes tested simultaneously). In the binocular test, the tested correction may be the same for the two eyes, or instead different for each of the two eyes.

The manner in which the operator assesses and interprets the responses given by the examined subject in order to validate or not the test underway is subjective, it depends on the operator and two different operators risk not treating in the same way responses that are nevertheless identical. An operator may be tempted to validate a response that is false but close to the correct response, for example "O" instead of "D" or "Q", etc. The consequence of this is that the performed visual acuity measurement is not very reliable.

A solution is thus sought enabling, within the context of an eyesight examination or a verification of a visual correction worn, to measure visual acuity in a more objective manner than in the prior art.

DESCRIPTION OF THE INVENTION

In this context, the invention aims to overcome all or part of the drawbacks of the prior art identified above.

For this purpose, a first aspect of the invention relates to a visual test method comprising a step of arranging an optical lens in a slot of a support and the following steps according to which a control module:
  displays one test symbol or a plurality of test symbols on a reading screen and on a selection screen and further displays one validation symbol at least on the selection screen;
  receives a selection of one test symbol or of the validation symbol on the selection screen;
the method being such that:
  when the control module receives a selection of one test symbol, the control module selects said test symbol by modifying at least one appearance characteristic of said test symbol in such a way that it changes from an initial appearance to a modified appearance which differentiates it from non-selected test symbols;
  when a first predetermined time has elapsed since the last selection of one test symbol or since the display of the test symbol or the plurality of test symbols, the control module modifies at least one appearance characteristic of the validation symbol;
the control module ends the visual test method as soon as a predetermined number of test symbols has been selected.

A second aspect of the invention relates to a control module for the implementation of the visual test method according to the first aspect of the invention, the control module having:
  means for displaying one test symbol or a plurality of test symbols on a reading screen and on a selection screen;
  means for displaying one validation symbol at least on the selection screen;
  means for receiving a selection of one test symbol or of the validation symbol on the selection screen;
the means for displaying on the selection screen and the reading screen and of the means for receiving a selection on the selection screen being such that:
  when the control module receives a selection of one test symbol, the control module selects said test symbol by modifying at least one appearance characteristic of said test symbol in such a way that it changes from an initial appearance to a modified appearance which differentiates it from non-selected test symbols;
  the control module modifies at least one appearance characteristic of the validation symbol, in such a way that it changes from an initial appearance to a modified appearance, when the first predetermined time has elapsed since the last selection of one test symbol or since the display of the test symbol or the plurality of test symbols;

the control module ends the visual test method as soon as a predetermined number of test symbols has been selected.

A third aspect of the invention relates to a system for the implementation of a visual test method according to the first aspect of the invention, comprising a control module according to the second aspect of the invention as well as a selection screen and a reading screen.

Apart from the characteristics that have been mentioned in the preceding paragraphs, the visual test method according to the first aspect of the invention, the control module according to the second aspect of the invention and the system according to the third aspect of the invention may have one or more complementary characteristics among the following, considered individually or according to all technically possible combinations thereof:

- when the first predetermined time has elapsed since the display of the test symbol or the plurality of test symbols, independently of the selection or absence of selection of one or more test symbols, the control module modifies at least one appearance characteristic of the validation symbol.
- When the control module receives a selection of one test symbol which is already selected, the control module deselects said test symbol while giving it back its initial appearance.
- The control module automatically ends the visual test method when a second predetermined time has elapsed since the modification of at least one appearance characteristic of the validation symbol by the control module.
- The validation symbol is a first validation symbol as long as no test symbol has been selected, or a second validation symbol, distinct from the first validation symbol, as soon as at least one test symbol is selected.
- Each test symbol is:
  - a letter, or
  - a figure, or
  - a drawing, or
  - a Snellen E, or
  - a Landolt C.
- The selection screen and the reading screen are two distinct screens.
- Alternatively, the selection screen and the reading screen are a single and same screen.

BRIEF DESCRIPTION OF THE FIGURES

Other characteristics and advantages of the invention will become clear on reading the description that follows, with reference to the appended figures.

For greater clarity, identical or similar elements are marked by identical reference signs in all of the figures.

DETAILED DESCRIPTION OF AT LEAST ONE EMBODIMENT OF THE INVENTION

A first aspect of the invention relates to a visual test method by means of a control module, making it possible to objectivise a visual acuity measurement. A second aspect of the invention relates to the control module for the implementation of the visual test method according to the first aspect of the invention. A third aspect of the invention relates to a system comprising the control module according to the second aspect of the invention, a selection screen and a reading screen, for the implementation of the visual test method according to the first aspect of the invention.

Within the scope of the present invention, "optical lens" is taken to mean an optical element of quality suited to the production of prescription glasses, without prejudicing the material of which it is made and which may notably be glass or plastic. The terms "ophthalmic lens" or "corrective lens" may also be employed. The term "optical lens" may be also employed strictly speaking, providing it is indeed interpreted in the sense of an optical element of quality suited to the production of prescription glasses, as opposed to a corneal lens or contact lens.

Method according to the First Aspect of the Invention

Figure 1A:
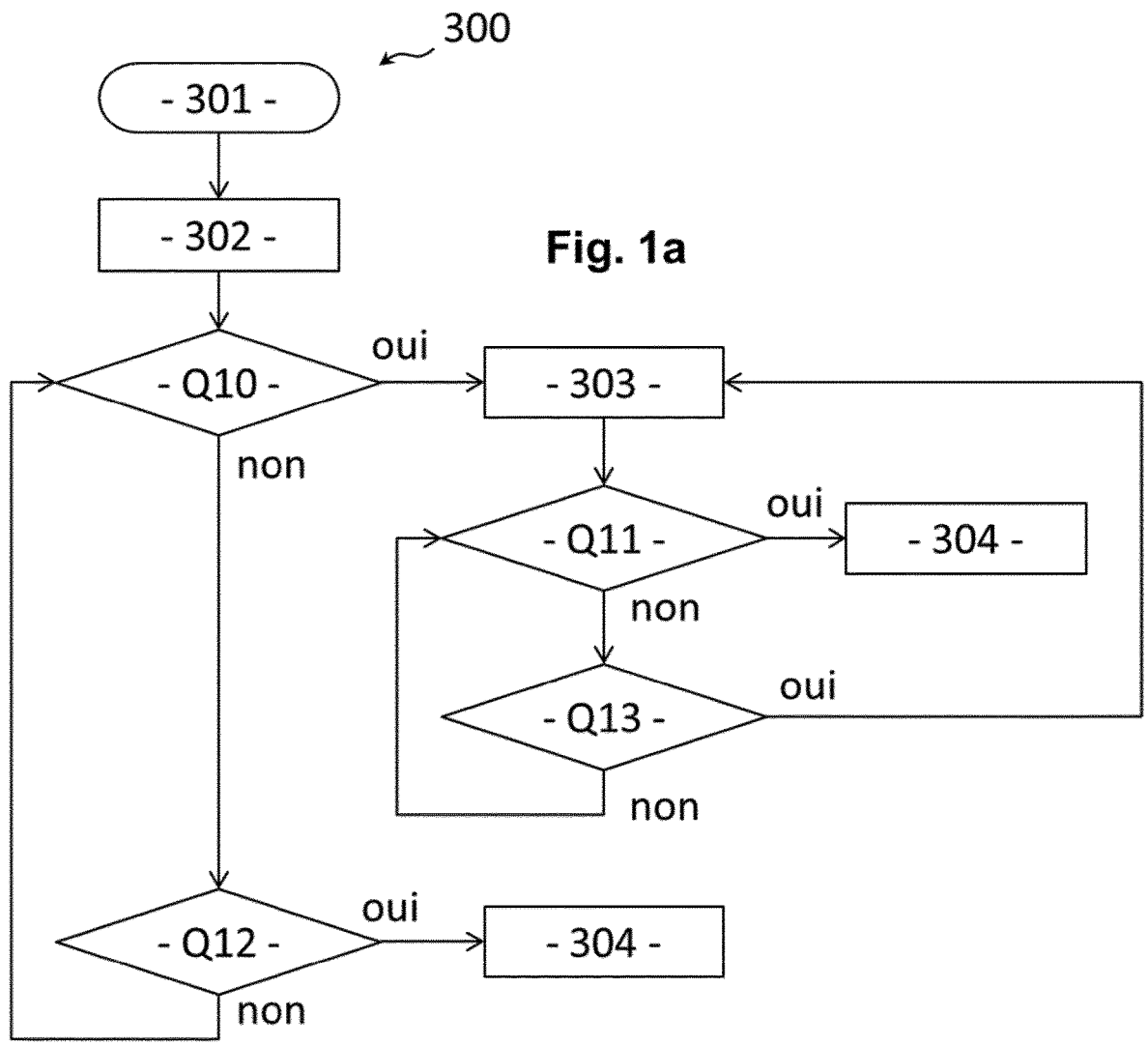
FIG. 1a shows a diagram of the steps of a first alternative of the visual test method according to the first aspect of the invention.
Figure 1B:
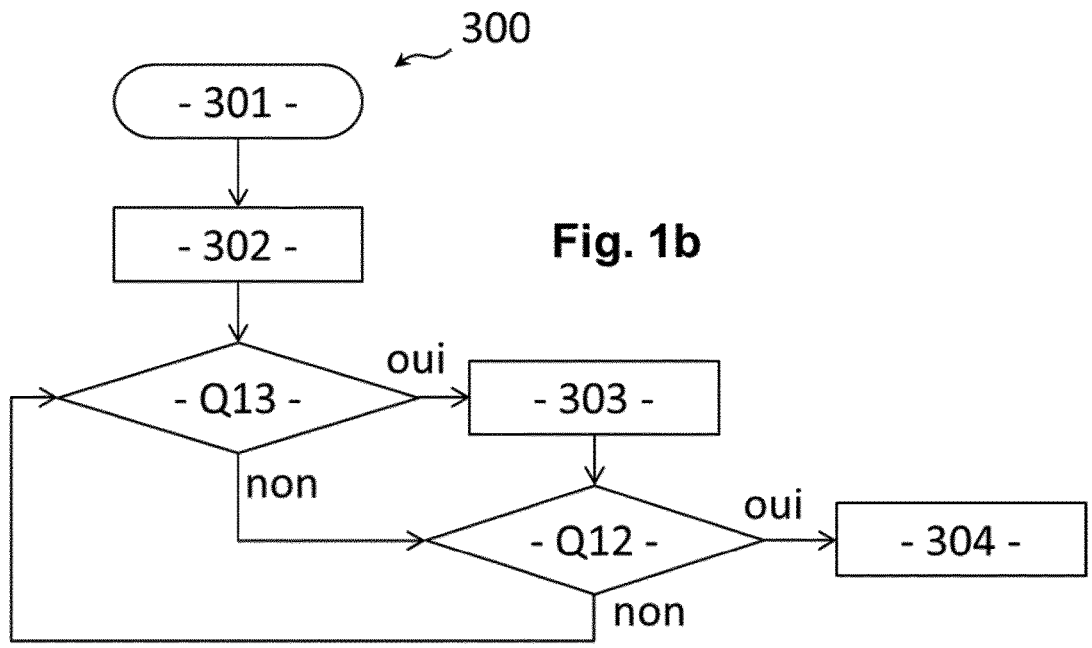
FIG. 1b shows a diagram of the steps of a second alternative of the visual test method according to the first aspect of the invention.

FIG. 1a shows a diagram of the steps of the method 300 according to a first alternative. The FIG. 1b shows a diagram of the steps of the method 300 according to a second alternative.

Hereafter, "an operator selects a symbol" is taken to mean the fact that the operator performs an action of selection of said symbol, in interaction with the selection screen. "The control module selects a symbol" is taken to mean the fact that the control module validates the selection received from the operator and modifies at least one appearance characteristic of said symbol in such a way that it changes from an initial appearance to a modified appearance which differentiates it from non-selected symbols. "The control module deselects a test symbol" is taken to mean the fact that the control module modifies said test symbol in such a way that it loses its modified appearance and recovers its initial appearance. "Selected test symbol" is taken to mean a test symbol selected both by the operator and by the control module, that is to say a test symbol for which the action of selection by the operator is validated by the control module. "Non-selected test symbol" is taken to mean a test symbol not selected by the operator (no selection action), or a test symbol selected by the operator and deselected by the control module, that is to say for which the operation of selection by the operator is interpreted as a deselection by the control module.

Figure 2:
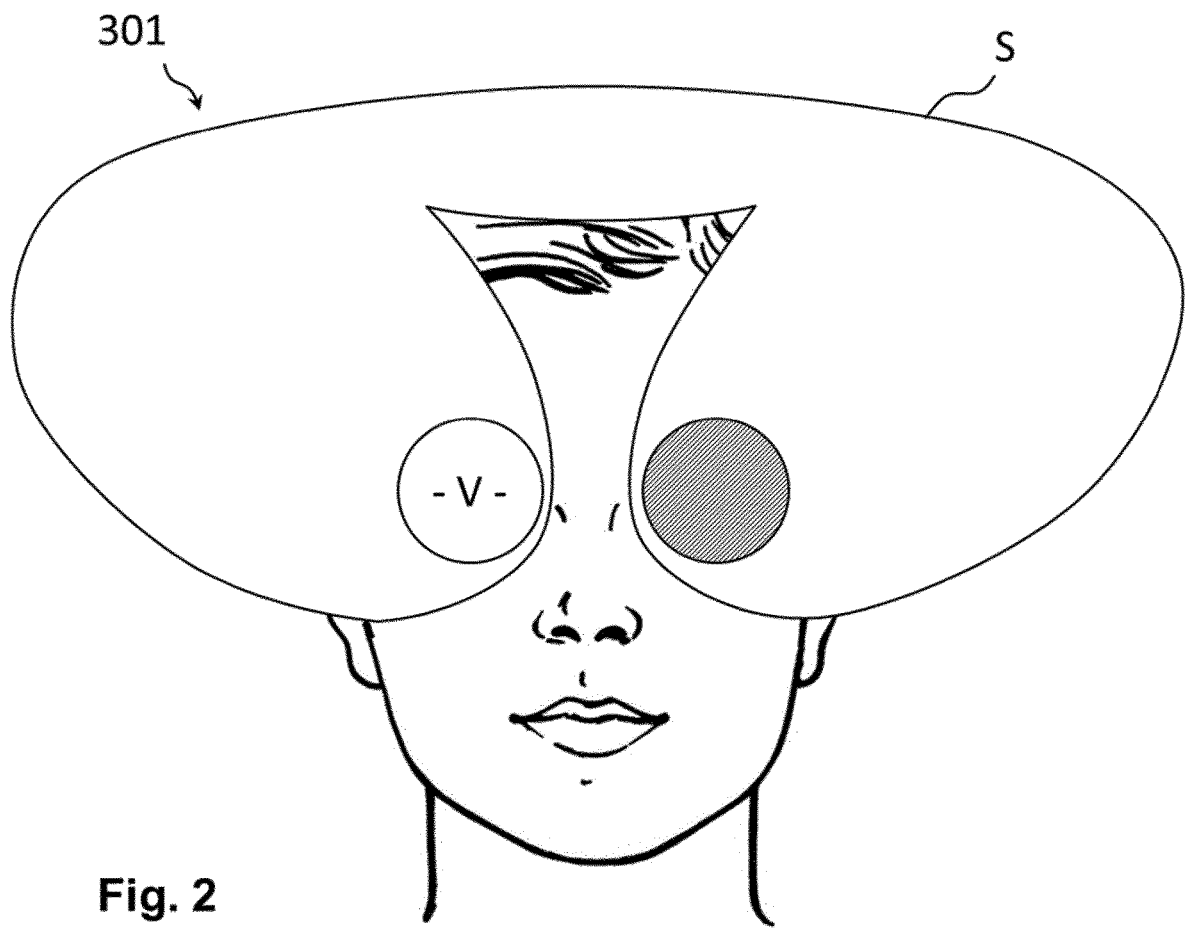
FIG. 2 shows an arrangement of an optical lens in a slot of a support, according to a first step of the visual test method according to the first aspect of the invention.

The first alternative of FIG. 1a will now be described. According to a first step 301 illustrated in FIG. 2, an optical lens V is arranged in a slot of a support S which is either a refractor head, automatic or manual, or a pair of test glasses. A refractor head or a pair of test glasses are both a support comprising first and second slots, one for each eye, each being able to receive an element which is either an opaque mask, or an optical lens. In the case of a pair of test glasses, the operator manipulates and manually arranges the different elements in the slots of the support. In the case of a refractor head, the operator does not directly manipulate the different elements: he arranges them in the different elements of the support by actuating thumbwheels in the case of a manual refractor head, or via a control console in the case of an automatic refractor head. The support is preferentially an automatic refractor head and, in this case, it is the control module according to the second aspect of the invention which ensures the function of "control console" of the automatic refractor head.

Within the scope of the present invention, "optical lens arranged in a slot of the support" is taken to mean either a single optical lens, or a combination of several optical lenses, enabling a certain optical correction to be made. The support is intended to be placed in front of the examined subject in such a way that the examined subject looks at, through the first and second slots, a reading screen on which at least one test symbol is displayed. A step of arranging an element in a slot may begin if appropriate by a step of removing a preceding element from said slot.

Within the scope of the visual test method according to the first aspect of the invention, the support is used in the right eye monocular test or in the left eye monocular test or in the binocular test. In the right eye monocular test, an optical lens is arranged in the slot corresponding to the right eye whereas a mask is arranged in the slot corresponding to the left eye. In the left eye monocular test, an optical lens is arranged in the slot corresponding to the left eye whereas a mask is arranged in the slot corresponding to the right eye. In the binocular test, an optical lens is arranged in each of the two slots; it may be a same optical lens, that is to say a same optical correction, in each of the two slots, or instead two different optical lenses, that is to say two different optical corrections, in each of the two slots.

Figure 3A:
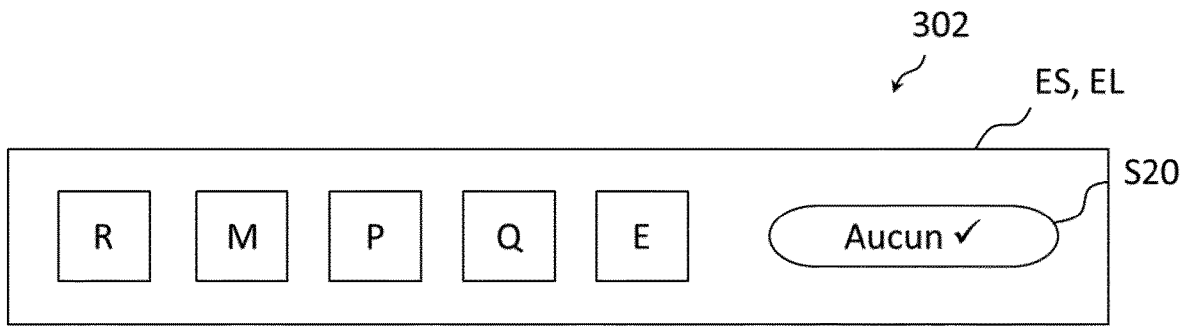
FIG. 3a shows a first example of display, only on a selection screen or both on a selection screen and a reading screen, of a plurality of test symbols and one validation symbol.

According to a second step 302 illustrated for example in FIG. 3a, the control module displays on a selection screen ES and on a reading screen EL, which are two distinct screens or alternatively a single and same screen, one test symbol or a plurality of test symbols. When a plurality of test symbols is displayed, it preferentially involves a plurality of test symbols distinct from each other. Each test symbol may be:
  a letter of the alphabet, or
  a figure, or
  a drawing, for example a car, a flower, a house, a cat . . . , or
  a Snellen E, also called Raskin trident, or a Landolt C, also called Landolt ring.

The type of test symbol is advantageously adapted to the profile of the examined subject: for example one or more test symbols of drawing type will be chosen if the examined subject is not able to read letters of the alphabet (young child), etc. The number of displayed test symbols varies preferentially from 1 to 7, with a preference for uneven numbers. In the example of FIG. 3a, five different letters of the alphabet are displayed: "R", "M", "P", "Q", "E".

During the second step 302, no test symbol is selected and all the test symbols preferentially have a same initial appearance. Still according to the second step 302, the control module further displays on the selection screen ES, or both on the selection screen ES and on the reading screen EL, one validation symbol which is preferentially a first validation symbol S20 when no test symbol is selected, the first validation symbol S20 indicating that no test symbol has been selected. FIG. 3a shows such an example of first validation symbol S20.

Figure 3B:
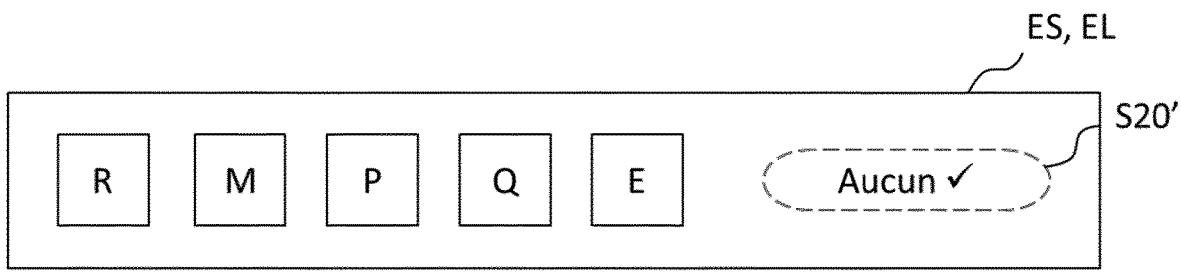
FIG. 3b shows a second example of display, only on a selection screen or both on a selection screen and a reading screen, of a plurality of test symbols and one validation symbol.
Figure 3C:
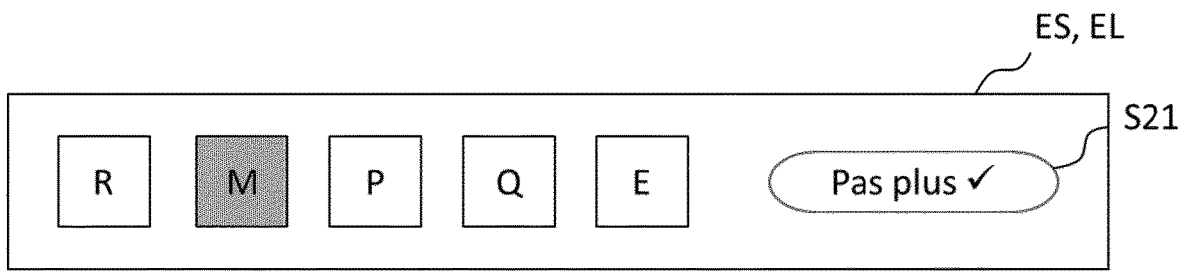
FIG. 3c shows a third example of display, only on a selection screen or both on a selection screen and a reading screen, of a plurality of test symbols and one validation symbol.

The method 300 next comprises a first decision Q10 according to which the control module responds to the question: "Has the control module received a selection of one first test symbol?".
  If yes, that is to say if the operator has selected one first test symbol and the control module has received the selection of said first test symbol by the operator, the control module selects said first test symbol according to a third step 303. The validation symbol is preferentially a second validation symbol S21 when at least one test symbol is selected thus the control module preferentially replaces the first validation symbol by the second validation symbol S21 as soon as the first test symbol is selected by the operator. FIG. 3c shows such a second validation symbol S21. Alternatively, the control module may display a same validation symbol independently of the selection or absence of selection of one or more test symbols. The method 300 next continues by a second decision Q11
  If no, that is to say if the operator has selected no test symbol, the method 300 continues by a third decision Q12.

According to the third decision Q12, the control module responds to the question: "Has a first predetermined time elapsed since the second display step 302?"
  If yes, according to a fourth step 304, the control module modifies at least one appearance characteristic of the validation symbol, in this particular case preferentially the first validation symbol S20. FIG. 3b shows such a modified first validation symbol S20'.
  If no, the method 300 continues by looping back on the first decision Q10.

Figure 3D:
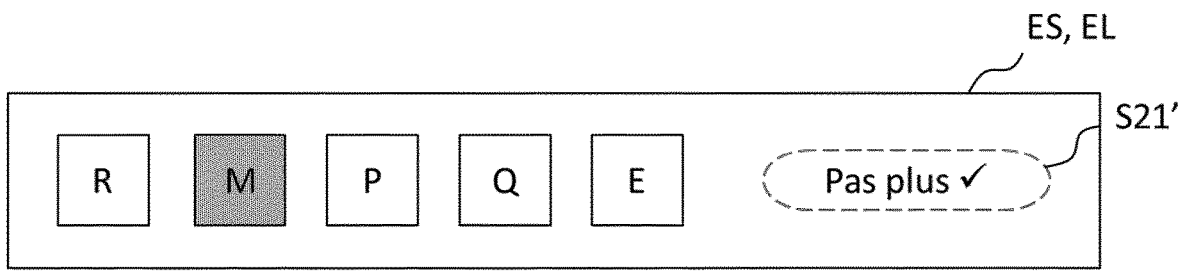
FIG. 3d shows a fourth example of display, only on a selection screen or both on a selection screen and a reading screen, of a plurality of test symbols and one validation symbol.

According to the second decision Q11, the control module responds to the question: "Has the first predetermined time elapsed since the last selection of one test symbol?"
  If yes, according to the fourth step 304, the control module modifies at least one appearance characteristic of the validation symbol, in this particular case preferentially the second validation symbol S21. FIG. 3d shows such a modified second validation symbol S21'.
  If no, the method 300 continues by a fourth decision Q13.

According to the fourth decision Q13, the control module responds to the question: "Has the control module received a selection of one new test symbol?".
  If yes, that is to say if the operator has selected one new symbol test and the control module has received the selection of said new test symbol by the operator, the method 300 loops back on the third step 303 according to which the control module selects said new test symbol. "New test symbol" is taken to mean a test symbol selected by the operator and/or the control module while at least one first test symbol is already selected.
  If no, the method 300 loops back on the second decision Q11.

According to the first alternative of the method 300 that has just been described, the control module calculates in the second decision Q11 whether the first predetermined time has elapsed since the last selection of one test symbol or, if no test symbol has been selected, calculates in the third decision Q12 whether the first predetermined time has elapsed since the display of the test symbol or the plurality of test symbols. According to the second alternative illustrated in FIG. 1b, the control module calculates in the second decision Q12 whether the first predetermined time has elapsed since the display of the test symbol or the plurality of test symbols, independently of the question of the selection or absence of selection of one or more test symbols.

The method 300 according to the second alternative thus comprises the first step 301 and the second step 302 such as described previously then the fourth decision Q13 according to which the control module responds to the question: "Has the control module received a selection of one new test symbol?". If yes, the method 300 continues with the third step 303 described previously then with the third decision Q12. If no, the method 300 continues directly with the third decision Q12. According to the third decision Q12, the control module responds to the question: "Has the first predetermined time elapsed since the second display step 302?" If yes, the method 300 continues with the third step 304 described previously. If no, the method 300 loops back on the fourth decision Q13.

According to a non-illustrated alternative of the method 300 according to any one of the alternatives thereof, the control module when it receives a selection of one test symbol responds to the question: "Has the test symbol selected by the operator already been selected by the control module?". If yes, the control module deselects said test symbol. If no, if the test symbol selected by the operator has not already been selected by the control module, the control module selects said test symbol.

Within the scope of the present application, a modification of at least one appearance characteristic of a test symbol may notably be:
   a change of colour, and/or
   a highlighting, and/or
   the addition of a framing or, if framing is already present, a modification of a type of framing line, etc.

Within the scope of the present application, a modification of at least one appearance characteristic of the validation symbol may notably be:
   a passage from a fixed display to a flashing display, and/or
   a change of dimensions and notably an increase in size of said validation symbol, and/or
   a change of colour, and/or
   a highlighting, and/or
   the addition of a framing or, if framing is already present, a modification of a type of framing line, etc.

FIGS. 3a, 3b, 3c and 3d show an example of a succession of different displays produced by the control module.
   In FIG. 3a, no test symbol is selected and the corresponding first validation symbol S20 is displayed. It involves for example the display of the second step 302.
   In FIG. 3b, the control module modifies the display of the validation symbol, in this particular case the first validation symbol S20 which becomes the modified first validation symbol S20', because the first predetermined time has elapsed, in the first alternative as in the second alternative, since the display of the second step 302 without any test symbol being selected.
   In FIG. 3c, the operator selects one first test symbol: for example the letter "M". The control module validates the selection of the operator and modifies the appearance of the first test symbol. The control module preferentially displays the second validation symbol S21.
   In FIG. 3d, the control module modifies the display of the validation symbol, in this particular case the second validation symbol S21 which becomes the modified second validation symbol S21', because the first predetermined time has elapsed, in the first alternative, since the selection of the first symbol without any new symbol being selected, or in the second alternative, since the display of the test symbol(s).

First and Second Predetermined Times

The control module modifies at least one appearance characteristic of the validation symbol as soon as a first predetermined time has elapsed. This makes it possible to incite the operator to select said validation symbol in order to end the method 300.

According to the first alternative of the method 300, the first predetermined time is calculated by the control module from the last selection of one test symbol or by default from the display of the test symbol or the plurality of test symbols according to the first alternative. In this case, the first predetermined time is preferentially comprised between two and five seconds.

According to the second alternative of the method 300, the first predetermined time is calculated by the control module systematically from the display of the test symbol or the plurality of test symbols, independently of the selection or absence of selection of one or more test symbols. In this case, the first predetermined time is preferentially comprised between two and nine seconds. The first predetermined time is advantageously chosen as a function of the number of test symbols displayed during the second step 302. Thus, the first predetermined time is preferentially comprised:
   between two and four seconds for a single displayed test symbol;
   between three and five seconds for two or three displayed test symbols;
   between five and eight seconds for four or five displayed test symbols;
   between six and nine seconds for six or seven displayed test symbols.

In the first alternative as in the second alternative, the first predetermined time is preferentially of the order of magnitude of the second, that is to say comprised in the interval [0.1 second; 20 seconds], more preferentially [0.1 second; 10 seconds], more preferentially [1 second; 10 seconds].

In the first alternative as in the second alternative, an increase in the first predetermined time may be provided according to the profile of the examined subject and notably according to his age, in particular if the examined subject is young, for example 10 years old or younger, or aged, for example 70 years old or older.

The increase in the first predetermined time may be independent of the first predetermined time, for example five additional seconds added to the first predetermined time whatever the first predetermined time, or a function of the first predetermined time, for example by doubling the first predetermined time.

According to any one of the alternatives of the method 300, when the first predetermined time has elapsed, the control module modifies at least one appearance characteristic of the validation symbol. According to an alternative of the method 300, when a second predetermined time, calculated by the control module from said modification of at least one characteristic of the validation symbol, has elapsed, the control module selects the validation symbol and automatically ends the method 300 according to the first aspect of the invention. The second predetermined time is preferentially comprised in the interval [10 seconds; 20 seconds]. The second predetermined time may be independent of the first predetermined time, for example equal to 15 seconds whatever the first predetermined time, or a function of the first predetermined time, for example comprised between two and five times the first predetermined time. An increase in the second predetermined time may also be provided as a function of the profile of the examined subject and notably as a function of his age, in the same way as for the first predetermined time. The increase in the second predetermined time may be independent of the second predetermined time or a function of the second predetermined time.

Predetermined Number of Test Symbols

The method 300 according to the first aspect of the invention ends as soon as a predetermined number of test symbols has been selected. This makes it possible to oversee the visual acuity measurement while avoiding that different successive operators choose different criteria to end the method 300. A ratio R of the number of test symbols selected over the number of displayed test symbols is defined. The predetermined number of test symbols is preferentially:
- one, for a single displayed test symbol—i.e. a ratio of 100%;
- one, for two displayed test symbols—i.e. a ratio of 50%;
- two, for three displayed test symbols—i.e. a ratio of 67%;
- three, for four displayed test symbols—i.e. a ratio of 75%;
- three, for five displayed test symbols—i.e. a ratio of 60%;
- four, for six displayed test symbols—i.e. a ratio of 67%;
- four, for seven displayed test symbols—i.e. a ratio of 57%.

Control Module according to the Second Aspect of the Invention

The control module according to the second aspect of the invention comprises for its part means for displaying simultaneously on the selection screen ES and on the reading screen EL one test symbol or a plurality of test symbols, as well as means for displaying one validation symbol on the selection screen ES only, or simultaneously on the selection screen ES and on the reading screen EL.

The control module according to the second aspect of the invention also comprises means for receiving a selection of one test symbol or the validation symbol on the selection screen ES.

Finally, the support is preferentially an automatic refractor head and, in this case, the control module according to the second aspect of the invention preferentially comprises means for ensuring the function of control console of the automatic refractor head, in particular to arrange an optical lens in a slot of the automatic refractor head.

Furthermore, the means for displaying on the selection screen ES and the reading screen EL and the means for receiving a selection on the selection screen ES are such that:
- when the control module receives a selection of one test symbol, the control module selects said test symbol by modifying at least one appearance characteristic of said test symbol in such a way that it changes from an initial appearance to a modified appearance which differentiates it from non-selected test symbols;
- the control module modifies at least one appearance characteristic of the validation symbol, in such a way that it changes from an initial appearance to a modified appearance, when a first predetermined time has elapsed since the last selection of one test symbol or since the display of the test symbol or the plurality of test symbols;
- the control module ends the visual test method as soon as a predetermined number of test symbols has been selected.

Generally speaking, the control module advantageously comprises means for implementing all or part of the optional steps of the method 300 according to the first aspect of the invention.

Selection Screen and Reading Screen

The operator interacts with the selection screen ES to select one test symbol or one validation symbol. The examined subject interacts for his part with the reading screen to identify, through the support, the displayed test symbol(s).

The selection screen ES and the reading screen EL may be two distinct screens or alternatively, a single and same screen fulfilling both the "selection" and "reading" functions. The display of the test symbol or the plurality of test symbols, of modified appearance in case of selection, is identical on the selection screen ES and on the reading screen EL in such a way that the operator and the examined subject access the same information. The display of the selection symbol is produced at least on the selection screen ES and preferentially both on the selection screen ES and on the reading screen EL in such a way that the operator and the examined subject access the same information.

Operator and Examined Subject

The operator is defined as being the person who interacts with the selection screen ES and thus with the control module. The operator is typically a practitioner, such as an ophthalmologist, an optician or even, within the scope of the present invention, an assistant without particular skills in the physics of refraction and the physiology of the visual system. The examined subject is defined as being the person who looks at the reading screen through the support. The examined subject is typically a patient or client of the practitioner.

The examined subject may himself be the operator. The examined subject may be the only operator in the absence of any practitioner. Alternatively, two distinct operators, for example the examined subject and a practitioner, may relay with each other. When the examined subject is the operator, either the reading screen forms a single and same screen with the selection screen, or the reading screen is a second selection screen.

System according to the Third Aspect of the Invention

The system according to the third aspect of the invention comprises the control module according to the second aspect of the invention as well as the selection screen ES and the reading screen EL.

The selection screen ES may be integrated with the control module. This is for example the case of a control module in the form of touch tablet or portable computer. Alternatively, the selection screen ES may be distinct from the control module. This is for example the case of a control module connected with a remote screen of computer screen, television screen or projection screen type.

The selection screen ES and the reading screen EL may be a single and same screen or two distinct screens.

Interaction Means

Each step of selection of one test or validation symbol is performed by the operator carrying out a selection action in interaction with the selection screen ES and thus with the control module. Each selection action may be carried out in different ways, of which several non-limiting examples are listed hereafter.

The selection action is preferentially carried out by means of a selection touch screen ES: the operator touches a zone of the screen on which is displayed a validation line or symbol in order to select said validation line or symbol.

Alternatively, the selection action may be carried out by means of an interface which is for example:

of mouse type: the operator positions the cursor of the mouse on the zone of the screen on which is shown the test or validation symbol and clicks on this zone in order to select said test or validation symbol; or of keyboard type: each test or validation symbol is identified by a key or combination of keys that is specific thereto, for example the key "R" for the first test symbol which is the letter "R", the key "M" for the second test symbol which is the letter "M", etc. A single and same key or combination of keys, for example the "entry" key, advantageously identifies the validation symbol. The operator presses on a key or combination of keys in order to select the corresponding test or validation symbol;

of directional handle or joystick type: each test symbol is identified by a direction that is specific thereto and the operator orients the handle in a given direction in order to select the corresponding test symbol. This alternative is particularly suited to test symbols characterizable by a direction, such as test symbols of "Snellen E" or "Landolt C" type: each Snellen "E" is characterised by the direction of its central bar, each Landolt "C" is characterised by the direction of its opening. The directional handle or joystick may advantageously have the shape of the displayed test symbol type, notably the form of a Snellen "E" or Landolt "C", in order to facilitate its orientation by the operator. The validation symbol is for its part preferentially identified by a button that is specific thereto and the operator presses on the button in order to select the validation symbol.

According to another alternative, the selection action is carried out by means of a voice control, via a microphone type equipment and a suitable module for processing the signal in the control module: each test or validation symbol is identified by a word or a group of words that is specific thereto, for example to say the letter "R" for the first test symbol which is the letter R, to say the letter "M" for the second test symbol which is the letter "M", etc. A single and same word or group of words, for example the word "validate" or "none", or "no other", etc., advantageously identifies the validation symbol. The operator says a word or group of words in order to select the corresponding test or validation symbol. This alternative is particularly suited to the case where the examined subject is the operator.

According to yet another alternative, the selection is made by means of a gestural control, via a camera type equipment and a suitable module for processing the signal in the control module. Each test or validation symbol is identified by a position or movement of the hand that is specific thereto, for example a clenched fist to select the validation symbol. The operator positions his hand or makes a movement in order to select the corresponding test or validation symbol. This alternative is particularly suited to test symbols, such as test symbols of "Snellen E" or "Landolt C" type, characterizable by a direction: for example the direction in which the central bar of each Snellen "E" points or the direction in which each Landolt "C" opens. The operator uses for example his raised thumb which he orients in a given direction in order to validate the corresponding test symbol.

The different selection actions of the method 300 according to the first aspect of the invention may all be carried out in a single and same manner, for example by means of a selection touch screen. Alternatively, a combination of several different techniques may be used to carry out the different selection actions of the method 300, for example the actions of selection of one test symbol via a selection touch screen or via a voice control, and the actions of selection of one validation symbol via a gestural control or a peripheral, etc.

The invention claimed is:

1. A visual test method comprising a step of arranging an optical lens in a slot of a support and the following steps according to which a control module:
   displays one test symbol or a plurality of test symbols on a reading screen and on a selection screen and further displays one validation symbol at least on the selection screen;
   receives a selection of one test symbol or of the validation symbol on the selection screen;
the method being such that:
   when the control module receives a selection of one test symbol, the control module selects said test symbol by modifying at least one appearance characteristic of said test symbol in such a way that the test symbol changes from an initial appearance to a modified appearance which differentiates it from non-selected test symbols;
   when a first predetermined time has elapsed since the last selection of one test symbol or since the display of the test symbol or the plurality of test symbols, the control module modifies at least one appearance characteristic of the validation symbol;
   the control module ends the visual test method as soon as a predetermined number of test symbols has been selected.

2. The method according to claim 1, wherein when the first predetermined time has elapsed since the display of the test symbol or the plurality of test symbols, independently of the selection or absence of selection of one or more test symbols, the control module modifies at least one appearance characteristic of the validation symbol.

3. The method according to claim 1, wherein when the control module receives a selection of one test symbol which is already selected, the control module deselects said test symbol, giving it back its initial appearance.

4. The method according to claim 1, wherein the control module automatically ends the visual test method when a second predetermined time has elapsed since the modification of at least one appearance characteristic of the validation symbol by the control module.

5. The method according to claim 1, wherein the validation symbol is a first validation symbol as long as no test symbol has been selected, or a second validation symbol, distinct from the first validation symbol, as soon as at least one test symbol is selected.

6. The method according to claim 1, wherein each test symbol is:
   a letter, or
   a figure, or
   a drawing, or
   a Snellen E, or
   a Landolt C.

7. A control module for the implementation of the visual test method according to claim 1, the control module having:
   means for displaying one test symbol or a plurality of test symbols on a reading screen and on a selection screen;
   means for displaying one validation symbol at least on the selection screen;
   means for receiving a selection of one test symbol or of the validation symbol on the selection screen;
the display means on the selection screen and the reading screen and the means for receiving a selection on the selection screen being such that:

when the control module receives a selection of one test symbol, the control module selects said test symbol by modifying at least one appearance characteristic of said test symbol in such a way that the test symbol changes from an initial appearance to a modified appearance which differentiates it from non-selected test symbols;

the control module modifies at least one appearance characteristic of the validation symbol, in such a way that the validation symbol changes from an initial appearance to a modified appearance, when the first predetermined time has elapsed since the last selection of one test symbol or since the display of the test symbol or the plurality of test symbols;

the control module ends the visual test method as soon as a predetermined number of test symbols has been selected.

8. A system for the implementation of a visual test method, comprising the control module according to claim 7 as well as the selection screen and the reading screen.

9. The system according to claim 8, wherein the selection screen and the reading screen are two distinct screens.

10. The system according to claim 8, wherein the selection screen and the reading screen are a single and same screen.

* * * * *